US00PP13288P2

(12) United States Plant Patent
Heims

(10) Patent No.: US PP13,288 P2
(45) Date of Patent: Nov. 26, 2002

(54) HEUCHERA PLANT NAMED 'BLACK BEAUTY'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/967,086

(22) Filed: Sep. 27, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Klarquist Sparkman, LLP

(57) ABSTRACT

A new and distinct hybrid of Heuchera plant characterized by shiny, deep maroon colored leaves with undulate margins.

1 Drawing Sheet

BOTANICAL CLASSIFICATION

Heuchera hybrid.

VARIETY DENOMINATION

'Black Beauty'.

BACKGROUND OF THE INVENTION

The present invention relates to a new and distinct cultivar of the herbaceous perennial, Heuchera, of the family Saxifragaceae, which originated from a cross between unknown parents. This new Heuchera was selected from seedlings grown from select interspecific hybrids that were open pollinated in the field in Canby, Oreg. Given its characteristics we know that *Heuchera americana* is in its parentage.

SUMMARY OF THE INVENTION

Deep maroon, glossy, ruffled leaves distinguish this new Heuchera hybrid from all others.

This new cultivar has been reproduced only by asexual propagation (division and tissue culture). Each of the progeny exhibits identical characteristics to the original plant. Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows Heuchera 'Black Beauty' growing in a pot in Canby, Oreg.

DETAILED PLANT DESCRIPTION

The following is a detailed description of the new Heuchera hybrid based on observations of two-year-old specimens grown in two-gallon containers in a greenhouse in Canby, Oreg. The color descriptions are all based on The Royal Horticultural Society Colour Chart.

Botanical name: Heuchera hybrid.
Market class: Herbaceous perennial.
Plant:
- *Form.*—Basal rosette.
- *Hardiness.*—USDA Zone 5 to 9.
- *Size.*—24 cm tall and 51 cm wide.
- *Habit.*—Rounded mound.

Leaf:
- *Type.*—Simple.
- *Arrangement.*—Rosette.
- *Shape.*—Ovate.
- *Lobing/division.*—5 to 7 lobes.
- *Venation.*—Palmate.
- *Margins.*—Undulate, crenate.
- *Apex.*—Mucronulate.
- *Base.*—Cordate, overlapping.
- *Blade size.*—9 to 12 cm long and 10 to 14 cm wide.
- *Vestiture.*—Sparsely scabrous.
- *Aspect.*—Glossy.
- *Texture.*—Waxy.
- *Petiole length.*—17 to 18 cm.
- *Petiole texture.*—Glandular puberulent.
- *Petiole color.*—Burgundy, between Greyed Purple 187B and 183A.
- *Leaf color.*—Topside — Deep maroon. In between Greyed Purple 187A and Black 202A. Bottom — Between Greyed Purple 187A and 187B with veins Red Purple 71A.

Inflorescence:
- *Type.*—Thyrse.
- *Number of flowers.*—About 100 per thyrse.
- *Peduncle.*—Unbranched. Height — 52 cm. Diameter — 0.15 cm. Color — Greyed Purple 187A. Texture — Glandular puberulent.
- *Pedicel.*—Length — 0.5 to 1 cm. Texture — Glandular puberulent. Color — Greyed Purple 183B.
- *Bloom period.*—June through July in Canby, Oreg.

Flower bud:
- *Size.*—0.2 cm.
- *Description.*—Glandular puberulent, ovoid, downfacing.
- *Color.*—Red Purple 59A.

Flower: Small, insignificant, wind-pollinated.
- *Type.*—Perfect, zygomorphic, downfacing.
- *Shape.*—Insignificant, campanulate.

*Size*.—0.4 cm long and 0.25 cm wide.
*Petal count*.—5, inconspicuous.
*Petal color*.—White 155D.
*Petal shape*.—Lanceolate with a clawed base.
*Petal size*.—0.2 cm long.
*Calyx*.—5 parted.
*Calyx size*.—0.3 cm deep and 2.5 cm wide.
*Calyx color*.—Pink with a brown tip. Greyed Orange 175A to Greyed Orange 174A to Greyed Purple 186C.
*Stamen number*.—5.
*Pistil color*.—Yellow Green 154D.
*Pollen color*.—No pollen, male sterile.
*Fragrance*.—None.
*Lastingness*.—Each thryse blooms for about 2 weeks on the plant.

Fruit:
*Type*.—Two-beaked ovoid capsule.
*Fertility*.—Low.
*Color*.—Tan. RHS 160C Greyed-Yellow to 199C Grey-Brown.

Seed:
*Shape*.—Linear.
*Size*.—2 mm. long.
*Color*.—Black. RHS 202A.

Disease tolerance: Excellent disease resistance to powdery mildew, the common problem of Heuchera.

Comparisons to similar Heuchera

Compared to *Heuchera americana* 'Palace Purple', an unpatented plant, Heuchera 'Black Beauty' has shinier, darker, more purple leaves that are more undulate.

Compared to Heuchera 'Ebony and Ivory' (U.S. Plant Pat. No. 11,380), Heuchera 'Black Beauty' has shinier, much darker, more ruffled leaves and wind rather than insect pollinated flowers (i.e. less showy flowers).

Compared to Heuchera 'Chocolate Ruffles' (U.S. Plant Pat. No. 8,965), this new cultivar has shinier, much darker foliage and its leaves are less cut and ruffled.

Compared to Heuchera 'Purple Petticoats' (EUBR #5885), this new cultivar has shinier, darker foliage.

I claim:

1. A new and distinct hybrid of Heuchera plant substantially as shown and described, characterized by shiny, deep maroon colored leaves with undulate margins.

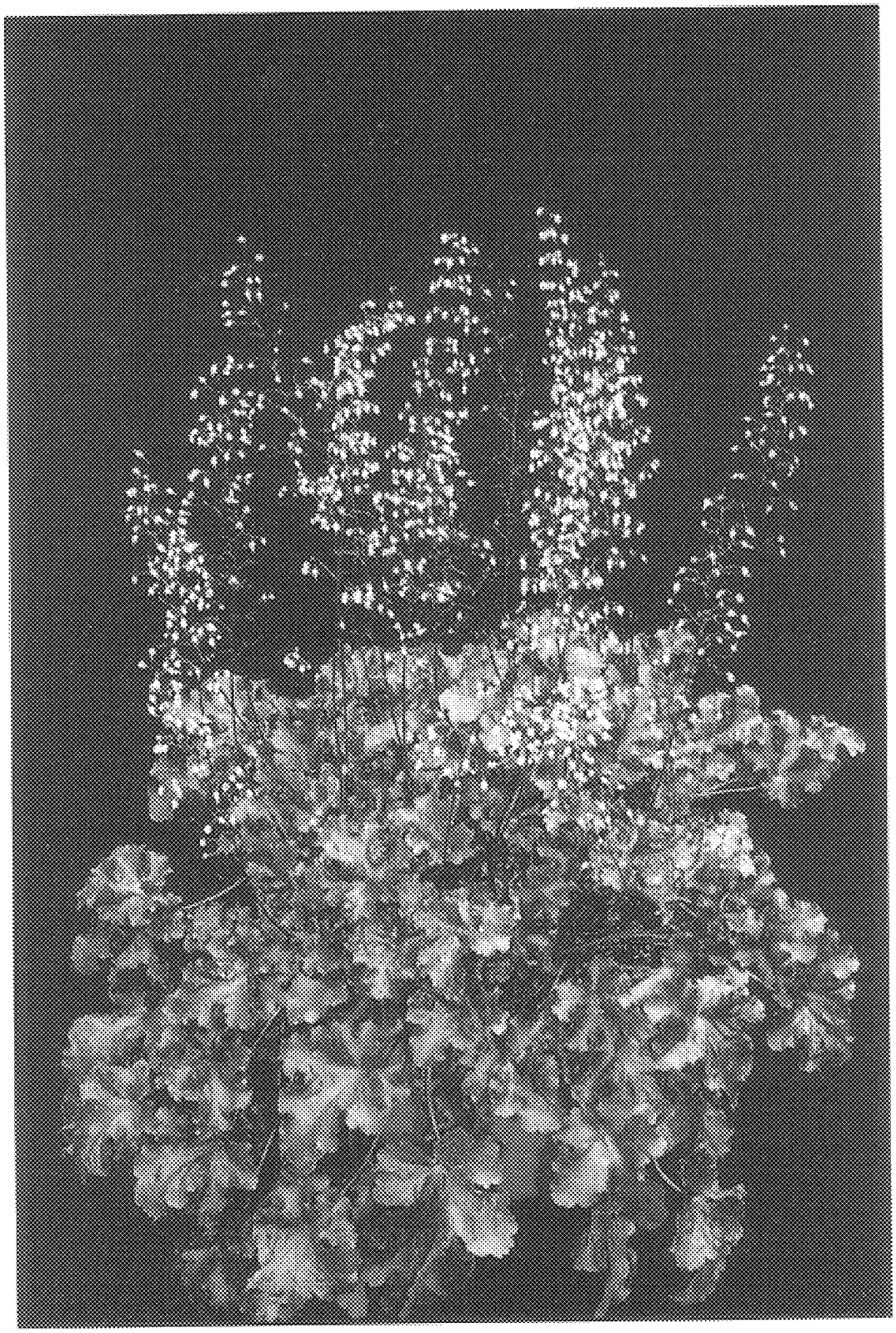

* * * * *